United States Patent
Baars et al.

(10) Patent No.: US 12,281,090 B2
(45) Date of Patent: Apr. 22, 2025

(54) PROCESS FOR PRODUCING 2,5-FURANDICARBOXYLIC ACID FROM ETHERS OF 5-HYDROXYMETHYLFURFURAL

(71) Applicant: Furanix Technologies B.V., Amsterdam (NL)

(72) Inventors: Hendrikus Jacob Baars, Amsterdam (NL); Jan Hendrik Blank, Amsterdam (NL); Jeffrey John Kolstad, Amsterdam (NL); Ana Sofia Vagueiro De Sousa Dias, Amsterdam (NL)

(73) Assignee: Furanix Technologies B.V., Amsterdam (NL)

( * ) Notice: Subject to any disclaimer, the term of this patent is extended or adjusted under 35 U.S.C. 154(b) by 445 days.

(21) Appl. No.: 17/778,921

(22) PCT Filed: Dec. 18, 2020

(86) PCT No.: PCT/EP2020/087052
§ 371 (c)(1),
(2) Date: May 23, 2022

(87) PCT Pub. No.: WO2021/123189
PCT Pub. Date: Jun. 24, 2021

(65) Prior Publication Data
US 2022/0411393 A1 Dec. 29, 2022

(30) Foreign Application Priority Data
Dec. 20, 2019 (EP) .................................. 19218642

(51) Int. Cl.
*C07D 307/68* (2006.01)
(52) U.S. Cl.
CPC .................. *C07D 307/68* (2013.01)

(58) Field of Classification Search
CPC .................................................... C07D 307/68
USPC .......................................................... 549/485
See application file for complete search history.

(56) References Cited

U.S. PATENT DOCUMENTS

| | | |
|---|---|---|
| 2019/0023838 A1 | 1/2019 | Janka et al. |
| 2019/0127342 A1 | 5/2019 | Huang et al. |

FOREIGN PATENT DOCUMENTS

| | | |
|---|---|---|
| WO | 2011/043660 A2 | 4/2011 |
| WO | 2014/014981 A1 | 1/2014 |
| WO | 2016/195499 A1 | 12/2016 |
| WO | 2016/195500 A1 | 12/2016 |

OTHER PUBLICATIONS

Notice of Reasons for Rejection, Japanese Office Action, Japanese Patent Application No. 2022-538254, dated Dec. 9, 2024, 9 pages.

*Primary Examiner* — Taylor V Oh
(74) *Attorney, Agent, or Firm* — Hoffmann & Baron, LLP

(57) ABSTRACT

A process for producing a carboxylic acid composition including 2,5-furandicarboxylic acid, including the steps: a) oxidizing an oxidizable compound including 5-alkoxymethylfurfural in an oxidation reactor in the presence of a saturated organic acid solvent having from 2 to 6 carbon atoms and a catalyst system comprising cobalt, manganese and bromine using an oxidizing gas at a temperature in the range of 160 to 210° C. to obtain a crude carboxylic acid composition including mono alkyl ester of 2,5-furandicarboxylic acid and solid 2,5-furandicarboxylic acid, b) isolating at least a portion of the solid 2,5-furandicarboxylic acid from the crude carboxylic acid composition in a solid-liquid separation zone to generate a solid cake and a mother liquor, c) determining the amount of manganese and/or cobalt in the cake, and d) increasing the amount of one or more controlling acids in the oxidation reactor.

21 Claims, No Drawings

PROCESS FOR PRODUCING 2,5-FURANDICARBOXYLIC ACID FROM ETHERS OF 5-HYDROXYMETHYLFURFURAL

CROSS-REFERENCE TO RELATED APPLICATIONS

This application is the National Stage of International Application No. PCT/EP2020/087052, filed Dec. 18, 2020, which claims the benefit of European Application No. 19218642.7, filed Dec. 20, 2019, the contents of which is incorporated by reference herein.

TECHNICAL FIELD

The present invention relates to a process for producing a carboxylic acid composition comprising 2,5-furandicarboxylic acid, specifically a process for producing a carboxylic acid composition comprising 2,5-furandicarboxylic acid using 5-alkoxymethylfurfural as starting material.

BACKGROUND 2,5-Furandicarboxylic acid (FDCA) is known in the art to be a highly promising building block for replacing petroleum-based monomers in the production of high performance polymers. In recent years FDCA and the novel plant-based polyester polyethylenefuranoate (PEF), a completely recyclable plastic with superior performance properties compared to today's widely used petroleum-based plastics, have attracted a lot of attention. These materials could provide a significant contribution to reducing the dependence on petroleum-based polymers and plastics, while at the same time allowing for a more sustainable management of global resources. Correspondingly, comprehensive research was conducted in the field to arrive at a technology for producing FDCA and PEF in a commercially viable way, in order to allow successful marketing of these promising materials.

FDCA is typically obtained as crude carboxylic acid composition by oxidation of molecules having furan moieties, e.g. 5-hydroxymethylfurfural (5-HMF) as well as the corresponding 5-HMF esters or 5-HMF ethers, e.g. 5-alkoxymethylfurfural, and similar starting materials, that are typically obtained from plant-based sugars, e.g. by sugar dehydration. A broad variety of oxidation processes is known from the prior art, that comprises e.g. enzymatic or metal catalysed processes.

One of the most established techniques in the field uses a catalyst system comprising cobalt, manganese and bromine to oxidize compounds having a furan moiety to FDCA using oxygen or air as an oxidizing agent. Respective processes that are applicable to a wide variety of starting materials are for example disclosed in WO 2014/014981 A1 or WO 2011/043660 A1.

As the purity obtainable for the crude carboxylic acid composition in the above-mentioned processes is oftentimes not sufficient for achieving the required degree of purity that is needed for the polymerisation of FDCA to PEF or other high performance polymers, purification processes have been developed for further purifying the crude carboxylic acid compositions in order to produce a purified carboxylic acid composition. These processes comprise e.g. hydrogenation steps, post oxidation steps, distillation steps, recrystallization steps or similar methods, oftentimes combined with comprehensive purification schemes with several steps of washing and isolating the obtained carboxylic acid composition. Exemplary purification processes are e.g. disclosed in WO 2014/014981 A1 or WO 2016/195499 A1.

In recent years it was discovered that one of the most promising approaches for arriving at FDCA in an economically viable fashion employs a significant amount of ethers of 5-HMF, e.g. 5-alkoxymethylfurfural, as starting material for the oxidation. As a result, the crude carboxylic acid composition obtained in such processes does not only comprise the free diacid, i.e. FDCA, but also includes a significant amount of the mono alkyl ester of FDCA, wherein currently those processes appear to be most established that employ 5-methoxymethylfurfural as the starting material for the oxidation and which result in significant amounts of the mono methyl ester of FDCA (FDCA-Me).

While some prior art documents are eager to report high yields and good purities for their claimed oxidation processes, less attention is often paid to the fact that the underlying reactions are in most cases very difficult to run in practice and/or are quite sensitive to external influences. This is particularly true for batch experiments with long residence times or (semi-) continuous process that need to be operated (in a preferably steady state) over a long time period. In particular, these difficulties are very severe if several subsequent process steps need to be chained together in order to arrive at the desired product, as a small deviation in one process step can potentially multiply its negative effect in downstream reactions.

Furthermore, in most prior art documents only laboratory scale experiments are disclosed. However, the production of a new compound in a commercially viable way requires large scale reactors that make it even more challenging to keep the reactions running. In a real industrial scale plant, gradients in process parameters like e.g. temperature and concentration, variations in mass flow rates of compounds or other influences can result in a process that stops entirely or produces undesired product. For example, the use of recycle streams in order to increase process efficiency or economy can lead to the build-up of materials, either desirable or undesirable.

Unfortunately, while the oxidation process that starts from 5-alkoxymethylfurfural as starting material has several benefits, e.g. efficient dehydration of sugar and product recovery to produce 5-alkoymethylfurfural, high yields and good product purity, over comparable prior art processes that do not yield mono alkyl esters of FDCA, such processes have proven to sometimes be particular difficult to control. When establishing the technology, it was found that it can be difficult to keep the processes running (the skilled person often calls such a process "alive" or "living") for a long time. For several sets of process parameters, several of which are reported to be preferred in the prior art based on lab scale experiments, the process tends to stop after some time, (the skilled person often calls such processes "dead" or "dying") and sometimes it is not even possible to initiate the process in the first place. While a dying oxidation process for producing FDCA can manifest itself in several ways, it is often observed that the colour of the resulting product, in most cases obtained as a solid cake, changes from white to yellow and further to brown, with FDCA yields dropping significantly, as more and more unwanted side products are produced. In consequence, the colour of the cake on the white to brown scale is a good qualitative indicator if the process left the desired regime and is running in an undesirable state or even is in the process of "dying" completely. Furthermore, the stop of the reaction can usually be evidenced by a rapid increase in the oxygen content of the outlet gas stream of the reactor, and a reduction in $CO_2$ and CO production.

In addition to the above described problems of oxidation processes that start from 5-alkoxymethylfurfural, it is unfortunately also observed, that these process are more likely than other prior art processes to suffer from an incorporation of catalyst metals into the product cake. This not only contaminates the product, but also withdraws valuable catalyst from the system that could otherwise be reused or recycled.

The incorporation of catalyst metals into the product cake appears to be particularly problematic with respect to the oxidation of furan containing moieties to form 2,5-furandicarboxylic acid. Although this problem has not been previously reported, to the inventors' knowledge, it manifests itself particularly strongly with respect to manganese incorporation into the cake. In such a case the product cake will be particularly enriched in manganese, relative to cobalt, in the cake compared to the catalyst feed. The inventors believe that this effect is different and distinct from the sometimes observed over-oxidation of manganese (II) to manganese (IV) which is sometimes reported in the Co/Mn/Br literature for organic acid production via oxidation, in which manganese is oxidized to form $Mn(IV)O_2$ which subsequently precipitates from solution as black specs, in the product cake. Observations made and reported here within show a phenomenon where a pink colour appears in the cake, and it is associated with an excess of manganese in the cake.

While not wishing to be bound by any theory, we believe that a relatively insoluble complex is formed between 2,5-furandicarboxylic acid and the manganese, possibly involving the doubly ionized form of the 2,5-FDCA and Mn(II).

The two effects described above, i.e. the challenge of keeping the process alive and the unfavourable tendency to incorporate metal from the catalyst system into the cake, appear to be two separate effects that are observed for oxidation processes that start from 5-alkoxymethylfurfural. For example, the incorporation of metal from the catalyst system is observed for "living" processes as well and qualitatively manifests itself through the cake having a pink colour. However, the two effects could potentially have a similar or at least a related origin. In any case, it is believed that the removal of catalyst from the process into the cake, i.e. the precipitate, will probably at least contribute to the difficulty of keeping the process alive, as running the process requires the metal catalyst.

DISCLOSURE OF THE INVENTION

In view of the above described problems, it was a primary objective to overcome the disadvantages of the prior art oxidation processes that use 5-alkoxymethylfurfural as starting materials, while maintaining the overall benefits of the basic process. In particular, there was a need for a process for producing 2,5-furandicarboxylic acid from 5-alkoxymethylfurfural that can reliably be initiated and operate for prolonged times without leaving the acceptable regime, or at least with a decreased likeliness of doing so, even when conducted at an industrial scale. Furthermore, there was a need for a process for producing 2,5-furandicarboxylic acid from 5-alkoxymethylfurfural that reduces the problem of incorporation of metals into the product cake. In particular, it was an objective to provide a process for producing 2,5-furandicarboxylic acid that allows influencing the running process in case that an elevated metal incorporation in the cake is observed, wherein it would be desirable that only minor adjustments are required, preferably to parameters that can be precisely controlled and quickly adjusted. It would be particularly desirable if the process for producing 2,5-furandicarboxylic acid could achieve the respective benefits by means of a sophisticated process control and without the need for additional substances or devices.

It was another objective to provide a process for producing 2,5-furandicarboxylic acid from 5-alkoxymethylfurfural that employs an optimized catalyst system that increases the robustness of respective processes and reduces the tendency for metal incorporation into the cake, while maintaining the beneficial properties that are reported for such processes.

Yet another objective was to provide a process for producing 2,5-furandicarboxylic acid that employs acetic acid, or acetic acid with minor amounts of water, as the primary washing fluid for the crude cake.

Without wishing to be bound to any theory, the presence of mono alkyl ester of 2,5-furandicarboxylic acid in the oxidation reactor seems to responsible for some of the beneficial effects that are typically associated with the respective technology in the prior art. Therefore, a minimum amount of mono alkyl ester of 2,5-furandicarboxylic acid in the oxidation reactor was found to be desirable. In particular, a certain amount of mono alkyl ester of 2,5furandicarboxylic acid in the feed to the oxidation reactor appears to reduce the tendency for manganese to appear in the product cake.

However, it was also found that the mono alkyl ester of 2,5-furandicarboxylic acid appears to be the reasons for some of the problems associated with the respective process that were described above. In particular, it seems that both the robustness of the process as well as the ability to wash metals out of the cake is adversely affected if the concentration of mono alkyl ester of 2,5-furandicarboxylic acid exceeds a maximum value. The solubility of the mono alkyl ester of 2,5-furandicarboxylic acid, e.g. monomethyl-2,5-furandicabroxylate, in acetic acid rich systems is much higher than the 2,5-furandicaroxylic acid. While the FDCA will crystallize extensively, with only a small residual remaining in solution, the FDCA-Me will tend to stay in solution with only a portion co-crystallizing into the product cake. As a result, the FDCA-Me will be retained in the "mother liquor" and will tend to accumulate in the system. If the level builds sufficiently, then it will exceed the solubility limit at the temperature used for product isolation, and a second phase of primarily FDCA-Me will crystallize out of the solution. We have found this precipitate to be particularly difficult to filter, consisting of a fluffy, waxy particle, which increases filtration time and which also makes cake washing difficult and which can lead to increased metals retention (in a ratio similar to the catalyst metal feed).

While not wishing to be bound by any theory, it is thought that the amount of mono alkyl ester of 2,5-furandicarboxylic acid needs to be kept within a specific range wherein the most expedient reference system for the concentration was found to be the mother liquor, i.e. the liquid that is obtained from the reaction mixture and the crude carboxylic acid composition after the FDCA was separated in a solid-liquid separation zone, as the mother liquor allows to gather information about the reaction medium in the oxidation reactor.

Correspondingly, in the process for producing a carboxylic acid composition comprising 2,5-furandicarboxylic acid of the present process, the mother liquor comprises mono alkyl ester of 2,5-furandicarboxylic acid in the range of 0.5 to 7% by weight with respect to the weight of the mother liquor.

However, we found that this limitation alone was not sufficient to completely eliminate the problem of metal incorporation from the catalyst into the cake. Fortunately, the inventors found a solution for controlling the process in a way that incorporation of metals into the cake can be countered at an early stage without the need for stopping the running process.

In the present process, the amount of manganese and/or cobalt in the cake is determined and only if the determined amount exceeds a predefined threshold value, an additional process step is conducted in order to adjust the process. Especially pronounced is the tendency for manganese to be incorporated into the cake, in a proportion greater than for cobalt. A useful measure of this tendency is the ratio of manganese to cobalt in the cake, divided by the ratio of manganese to cobalt in the catalyst feed. When this ratio has a value of about 1.0 the metals in the dry cake exactly reflect those in the catalyst system. When this ratio is significantly higher than 1, say 2 or higher, then manganese is being preferentially sequestered into the cake and a remedial control action as described herein should be undertaken.

We surprisingly found that the incorporation of metals into the cake can be countered if the amount of one or more controlling acids in the oxidation reactor is increased, wherein comprehensive experiments revealed that the one or more controlling acids need to be selected from the group consisting of hydrobromic acid and mono- or dicarboxylic acids having from 2 to 5 carbon atoms and a pKa of less than 3.2 for the process to operate properly.

Furthermore, we discovered that for an oxidation process that will yield mono alkyl ester of 2,5-furandicarboxylic acid, specific temperatures are required in order to allow for a reasonable operation, wherein a specific catalyst system was identified that has proven to be particular robust and in itself reduces the tendency of metal incorporation into the cake even in the presence of larger amounts of mono alkyl ester of 2,5-furandicarboxylic acid.

The invention relates to a process for producing a carboxylic acid composition comprising 2,5-furandicarboxylic acid, comprising the steps:
  a) oxidizing a oxidizable compound comprising 5-alkoxymethylfurfural in an oxidation reactor in the presence of a saturated organic acid solvent having from 2 to 6 carbon atoms and a catalyst system comprising cobalt, manganese and bromine using an oxidizing gas at a temperature in the range of 160 to 210° C. to obtain a crude carboxylic acid composition comprising mono alkyl ester of 2,5-furandicarboxylic acid and solid 2,5-furandicarboxylic acid,
  b) isolating at least a portion of the solid 2,5-furandicarboxylic acid from the crude carboxylic acid composition in a solid-liquid separation zone to generate a solid cake and a mother liquor,
  c) determining the amount of manganese and/or cobalt in the cake, and
  d) increasing the amount of one or more controlling acids in the oxidation reactor, if the determined amount of manganese and/or cobalt in the cake exceeds a predefined threshold value, wherein the one or more controlling acids are selected from the group consisting of hydrobromic acid and mono- or dicarboxylic acids having from 2 to 5 carbon atoms and a pKa of less than 3.2, and
wherein the mother liquor comprises mono alkyl ester of 2,5-furandicarboxylic acid in the range of 0.5 to 7% by weight with respect to the weight of the mother liquor.

With the present process it is possible to overcome the disadvantages of the prior art oxidation processes, while using ethers of 5-HMF as starting materials and maintaining the overall benefits associated with this technology, e.g. high yields, good product purities and availability of cheap starting materials. The process of the present invention can reliably be initiated and operated for a long time without leaving the acceptable regime of product quality, even when conducted as an industrial scale. With the process of the present invention, the problem of metal incorporation into the product cake can be addressed. As soon as the amount of metal in the cake exceeds a predefined threshold, a suitable counter measure is defined that directly allows for adjusting the process to yield a product cake with reduced amount of metals in the cake. In the process according to the invention, only a comparably minor intervention is required for the process control, wherein the addition of controlling acid can be precisely controlled and the intensity of the intervention, if required, can quickly be adjusted.

MODES FOR CARRYING OUT THE INVENTION

Step a) of the present process corresponds to a typical oxidation reaction for obtaining FDCA, wherein the temperature was defined to be in the range that was found to be particular beneficial for the production of FDCA from the starting material and particular suitable for allowing a process control that employs controlling acid. Likewise, the temperature was found to ensure that sufficient mono alkyl ester of 2,5-furandicarboxylic acid is formed. Furthermore, the oxidizable compound that is oxidized in step a) as a starting material is defined to be 5-alkoxymethylfurfural, i.e. an ether of 5-hydroxymethylfurfural.

The prior art also has many cases where lower oxidation temperatures are employed. However, the current process is to be preferred, as the higher temperatures allow the oxidation reactor to be run under an elevated pressure while still allowing the large heat generated by the oxidation reaction to be removed by vaporization. This is known to one skilled in the art as "adiabatic" operation, which is a means of saying that the heat of the reaction is not being removed by external sources such as coolers, loss through the walls, and the like. In general, the higher temperature requires a higher pressure operation for "adiabatic" operation. A higher pressure, in turn, allows for a higher oxygen partial pressure (at a proscribed oxygen volume %) in the reactor and reduces the risk of oxygen starvation. The oxygen volume percent in the off-gas is generally limited for safety reasons to be below the lower explosive limit, e.g. at a level of 10 vol %, or more preferably below about 6 vol %, to allow a margin of safety. This results in the formation of a crude carboxylic acid composition comprising mono alkyl ester of 2,5-furandicarboxylic acid and 2,5-furandicarboxylic acid. In the process according to the invention, the catalyst system for the oxidation comprises cobalt, manganese and bromine, wherein these compounds are preferably provided as cobalt acetate, manganese acetate and hydrobromic acid, wherein the usage of hydrobromic acid is especially preferred.

The oxidation reactor can be any typical oxidation reactor that is known in the art. The saturated organic acid solvent that is employed in the reaction has from 2 to 6 carbon atoms, wherein acetic acid is especially preferred.

In step b) at least a portion of the solid 2,5-furandicarboxylic acid is isolated, that means separated from the crude carboxylic acid composition, wherein the isolation is conducted in a solid-liquid separation zone.

Within the framework of the present invention the term at least a portion preferably means at least 10% by weight with respect to the weight of the crude carboxylic acid composition, more preferably at least 50% by weight, most preferably at least 80% by weight.

In the solid-liquid separation zone, a solid cake and a mother liquor are generated.

In step c) of the process of the present invention the amount of manganese and/or cobalt in the cake is determined. Preferably the amount of manganese is determined. The skilled person understands that the cake that comprises solid FDCA can be wet due to the presence of residual mother liquor. However, the skilled person that intends to determine the amount of a compound in the cake will either sufficiently dry the respective cake in order to be confident about the measurement result, or will adjust or correct the measurement and its result for the residual amount of mother liquor, respectively.

Preferably, the cake in step c) comprises more than 90% solids, more preferably more than 95% solids, most preferably more than 99% solids, by weight with respect to the weight of the cake, wherein the latter is also called "dry cake". The "moisture" content of the cake can be determined using any of several techniques known in the art, for example, by weight loss under controlled conditions of heating, and the results of the metals determination reported on a "moisture free" basis.

The amount of manganese and/or cobalt in the cake can be determined using any suitable measurement technique, wherein the respective techniques are well known to the skilled person, e.g. appropriately calibrated x-ray fluorescence (XRF) or inductively coupled plasma (ICP). Aside from chemical analysis, spectroscopic and optical measurement methods are especially preferred. In the most basic case, the amount of manganese in the cake is determined via optical inspection of the cake by the process operator, wherein the colour of the obtained cake is evaluated with respect to the intensity of pink colour, that is now-known to be typically associated with manganese in the cake in the oxidation of furfural related compounds to form FDCA.

If the determined amount of manganese and/or cobalt, preferably manganese, exceeds a predefined threshold value, e.g. because the cake was found to be too pink, the amount of one or more controlling acids in the oxidation reactor tends to be increased.

The term controlling acids is arbitrarily chosen to clearly denote the group of specific acids that were found suitable in the present process.

Suitable threshold values are defined by the skilled person based on the individual process characteristics and the amount of metals that are considered acceptable in the cake for subsequent processing steps and/or for further applications.

We have found that besides the total concentration of catalyst metals in the cake, which can also be influenced by retention of the catalyst-rich mother liquor, the enrichment of manganese, relative to cobalt, in the cake relative to the feed catalyst is also a suitable indicator. This ratio is particularly useful as applicants have found that in the oxidation of furfural related compounds to form FDCA with a catalyst system comprising cobalt, manganese and bromine, it is the manganese which is the most sensitive indicator of a problem and which is seen at unusually high levels in the cake. A manganese enrichment factor has been developed, which is defined according to the following equation:

$$(Mn/Co)_{cake}/(Mn/Co)_{catalyst}$$

This equation has the advantage of being unaffected by the absolute levels of catalyst or by the presence of for example, washing liquids, while reflecting the unwanted enrichment of manganese in the cake. A value of unity or less shows no preferential enrichment of manganese in the cake. For practical reasons, when absolute manganese contents are low, e.g. less than about 10 ppm in the cake, the value can fluctuate to as high as about 1.5. Values above that level, or for example above 2.5, indicate unwanted incorporation of manganese into the cake and call for a corrective action. Correspondingly, preferred is a process wherein the ratio of the weight ratio of manganese to cobalt in the cake to the weight ratio of manganese to cobalt in the catalyst system is less than 2.5, preferably less than 2, more preferably less than 1.5.

As defined above, the one or more controlling acids are selected from the group consisting of hydrobromic acid and mono- or dicarboxylic acids having from 2 to 5 carbon atoms and a pKa of less than 3.2. Hydrobromic acid is specifically preferred and was among the first controlling acids that were identified by the inventors, as it is oftentimes available at the plant as part of the catalyst system typically employed in step a). However, additional organic acids where tested and the inventors found that only those acids can function as controlling acids that have a certain acidity. It was found that the pKa of suitable controlling acids should be less than 3.2, wherein the pKa is measures in water.

Furthermore, it was confirmed in screening experiments, that apparently only mono- or dicarboxylic acids can serve as controlling acid, as higher poly carboxylic acids can cause a loss of activity, potentially due to complex formation. For example, trimellitic acid and pyromellitic acid, are relatively strong aromatic polycarboxylic acids, with first pKa values of 2.52 and 1.92, respectively. However, these acids can cause a loss of activity in certain oxidations, and are not suitable as controlling acids. It was found in the present work that FDCA, a relatively strong aromatic dicarboxylic acid, can also cause a loss of activity or failure of the system to initiate. This effect is not observed, to our knowledge, in oxidation of p-xylene to produce terephthalic acid. While not wishing to be bound by theory, the applicants speculate that the higher solubility of FDCA and its' higher acidity are at least partially responsible for this effect. Higher temperature oxidation amplifies this problem due to significantly increased solubility at higher temperatures and the resulting availability of the diacid to complex with catalyst components.

The mono methyl ester of FDCA, a mono carboxylic acid with the required pKa but 7 carbon atoms, can provide the desired effect when added as controlling acid. The monoester of FDCA, however, tends to build up in a recycle operation and at high levels has been found to have a detrimental effect on the oxidation, leading to slower reaction rates and more intermediates, and a brown colour or even a reaction which dies. Furthermore, the monoester of FDCA can lead to filtration difficulties and difficulty in removing the mother liquor from the cake, leading to higher overall metal levels. However, surprisingly, the mono carboxylic acid FCA, i.e. 2-furancarboxylic acid, was found to be a very suitable controlling acid for the process of the present invention. When FCA is used, however, the purification system used subsequent to the oxidation must be capable of removing it from the FDCA composition, if the FDCA is desired for use in polymerization. Correspondingly, the inventors deducted that controlling acids can be defined to be hydrobromic acid and mono- or dicarboxylic acids having from 2 to 5 carbon atoms and a pKa of less than 3.2. In the framework of the present invention, monoester of FDCA, which also functions like a controlling acid, is considered separately due to the special problems associated with its build-up, and so is limited to a range of use.

In step d) the amount of the one or more controlling acids is increased by deliberate and purposeful addition of one or more controlling acids into the oxidation reactor. Any in-situ formation of a controlling acid that could potentially occur in the oxidation reactor is not considered a deliberate and purposeful addition of one or more controlling acids and does not correspond to increasing the amount of one or more controlling acids in the oxidation reactor. As hydrobromic acid is oftentimes used to provide bromine ions to the catalyst of the oxidation reaction, it is expedient to discuss what is considered an increase of hydrobromic acid within the framework of the present invention. Most (semi-)continuous processes add additional catalyst, that oftentimes includes additional hydrobromic acid, in order to make up for the loss of bromine during the reaction, that is e.g. lost in the overhead or the mother liquor, in order to maintain the desired catalyst concentrations. The addition of hydrobromic acid to the oxidation reactor in order to maintain the desired hydrobromic acid concentration in the oxidation reactor does not constitute an increasing the amount of hydrobromic acid within the meaning of the present invention. In other words, step d) would require that the catalyst composition in the reactor is changed by increasing the bromine to metal ratio. Correspondingly, step d) of the process of the present invention could be:

d) increasing the amount of one or more controlling acids in the oxidation reactor or increasing the bromine to metal ratio in the catalyst system, preferably to weight ratios of larger than 2, even more preferably to weight ratios larger than 2.5, if the determined amount of manganese and/or cobalt in the cake exceeds a predefined threshold value, wherein the one or more controlling acids are selected from the group consisting of mono- or dicarboxylic acids having from 2 to 5 carbon atoms and a pKa of less than 3.2.

In other words, if the cake using the existing catalyst system was found to be high in metals, especially manganese, and the catalyst composition was then changed to increase the bromine level via addition of HBr, such a change would constitute an increasing the amount of a controlling acid within the meaning of the present invention. In clear contrast, increasing bromine via, e.g. NaBr or $NH_4Br$ would not constitute and increase, as these are not controlling acids within the meaning of this invention.

The skilled person is aware of several suitable methods for adjusting the concentration of mono alkyl ester of 2,5-furandicaroxylic acid in the oxidation reactor and correspondingly in the mother liquor to the level defined above. Among the options that are known in the art, the skilled person chooses an appropriate option based on his general knowledge. For example, the skilled person can increase the amount of solvent or other starting materials, in order to dilute the solution in the oxidation reactor, or, if a mother liquor recycle is employed, the skilled person can deliberately remove the mono alkyl ester of 2,5-furandicarboxylic acid from the mother liquor stream in order to alter the concentration of the ester in the oxidation reactor and in the fresh mother liquor. A portion of the mother liquor can also be removed, or purged, from the system in order to reduce the concentration of monoester and/or controlling acids. If a portion of mother liquor is purged, the acetic acid can still be recovered, for example by distillation, and the residue either discarded or treated to recover catalyst for recovery and reuse.

However, we found other convenient options for decreasing the amount of mono alkyl ester of 2,5-furandicarboxylic acid in the mother liquor, that otherwise tends to build up under certain conditions. It was found that a convenient way of decreasing the amount of the respective substance is available by increasing the temperature in the oxidation reactor of step a) and/or by increasing the residence time of the crude carboxylic acid in the oxidation reactor of step a) and/or by applying a post oxidation step a1) after step a) and/or by decreasing the temperature in the solid-liquid separation zone. A post-oxidation step has been found to be especially effective when employed at high temperature.

In view of this observation, a preferred embodiment of the present process comprises controlling, preferably decreasing, the amount of mono alkyl ester of 2,5-furandicarboxylic acid in the mother liquor, by increasing the temperature in the oxidation reactor of step a) and/or by decreasing the temperature in the solid-liquid separation zone and/or by increasing the residence time of the crude carboxylic acid in the oxidation reactor of step a) and/or by applying a post oxidation step a1) after step a), wherein the post oxidation is conducted in a post oxidation reactor under conditions as described for step a).

Most preferred is a process wherein the temperature in step a) is 170° C. or higher and wherein a post oxidation step a1) is applied after step a), wherein the post oxidation is conducted in a post oxidation reactor under conditions as described for step a). This process is especially preferred, as it was found that the amount of mono alkyl ester of FDCA in this case tends to plateau, that means it rises only up to a certain level, wherein this level was found to be well within the desired range defined above.

In fact, this observation has proven to be very useful for operating several processes that start from ethers of 5-HMF, independent of the problem of metal incorporation. Correspondingly, disclosed herein is a process for producing a carboxylic acid composition comprising 2,5-furandicarboxylic acid, comprising the steps:

a) oxidizing a oxidizable compound comprising 5-alkoxymethylfurfural in an oxidation reactor in the presence of a saturated organic acid solvent having from 2 to 6 carbon atoms and a catalyst system comprising cobalt, manganese and bromine using an oxidizing gas at a temperature in the range of 170 to 210° C. to obtain a crude carboxylic acid composition comprising mono alkyl ester of 2,5-furandicarboxylic acid and solid 2,5-furandicarboxylic acid, a1) oxidizing the crude carboxylic acid composition of step a) in a post oxidation reactor in the presence of a saturated organic acid solvent having from 2 to 6 carbon atoms and a catalyst system comprising cobalt, manganese and bromine using an oxidizing gas at a temperature in the range of 170 to 210° C. to obtain a raw carboxylic acid composition comprising mono alkyl ester of 2,5-furandicarboxylic acid and solid 2,5-furandicarboxylic acid, b) isolating at least a portion of the solid 2,5-furandicarboxylic acid from the raw carboxylic acid composition in a solid-liquid separation zone to generate a solid cake and a mother liquor, c) determining the amount of manganese and/or cobalt in the cake, and d) increasing the amount of one or more controlling acids in the oxidation reactor, if the determined amount of manganese and/or cobalt in the cake exceeds a predefined threshold value, wherein the mother liquor comprises mono alkyl ester of 2,5-furandicarboxylic acid in the range of 0.5 to 7% by weight with respect to the weight of the mother liquor.

Preferred is a process wherein the one or more controlling acids are selected from the group consisting of hydrobromic acid, bromoacetic acid, dibromoacetic acid, 5-bromo-2-furoic acid, fumaric acid, acetoxy-acetic acid, maleic acid and furoic acid. More preferably, the controlling acid is selected from the group consisting of hydrobromic acid, bromoacetic acid, dibromoacetic acid, acetoxy-acetic acid and 5-bromo-2-furoic acid. More preferably, the controlling acid is selected from the group consisting of bromoacetic acid, dibromoacetic acid, acetoxy-acetic acid and 5-bromo-2-furoic acid.

The above process is preferred, because the respective controlling acids were found to provide a particular good and pronounced effect, while at the same time being either comparably cheap and good to handle, or are available as waste and/or by-products of the process according to step a) and can be obtained on in the mother liquor of step b). Most preferably, a mixture of controlling acids is added to the oxidation reactor that comprises bromoacetic acid, dibromoacetic acid, acetoxy-acetic acid and 5-bromo-2-furoic acid. It is also preferred that the controlling acids are relatively stable, i.e. resistant to chemical decomposition, so as to not need frequent replenishment.

Preferred is a process according to the invention, wherein the process of producing a carboxylic acid composition is a continuous or semi-continuous process, preferably a continuous process, wherein at least a portion, preferably at least 60% by weight, more preferably at least 80% by weight, of the mother liquor is routed from the solid-liquid separation zone to the oxidation reactor as recycled mother liquor stream, wherein preferably the portion of mother liquor which is not routed to the oxidation reactor as recycled mother liquor stream is treated in an evaporation step to recover the organic acid solvent as a condensed vapor stream and/or wherein preferably one or more bases are added to the mother liquor which is treated in the evaporation, preferably in an amount which is equal to or greater than the amount of free bromide ions in the mother liquor, on a molar basis.

The process of the present invention provides acceptable results for batch processes, wherein e.g. a sample of the crude carboxylic acid composition comprising the solid precipitate is taken from the batch reactor, and processed in a solid-liquid separation zone according to step b). If required, controlling acids can be added to the oxidation reactor of the running batch process. Likewise, it is possible to complete a first batch process in order to analyze the resulting product cake and to provide additional controlling acids to the second batch run in case that the amount of metal in the cake of the first run exceeds the predefined threshold value.

However, the above defined process is clearly preferred, as the process of the present invention shows its full potential in continuous or semi-continuous processes, as these processes are in need for suitable controlling mechanisms that allow for a minimal invasive adjustment of the running system that is suitable to counter the problem of metal incorporation into the cake. Such processes generally involve continuous or intermittent addition of oxidizable compound and withdrawal of carboxylic composition comprising 2,5-furandicarboxylic acid. Beneficially, it is possible to reuse the mother liquor obtained in step b) in a subsequent run of batch experiments in order to increase the amount of controlling acids in the oxidation reactor. However, the design of the process of the present invention as a continuous or semi-continuous process allows routing the mother liquor from the solid liquid separation zone back to the oxidation reactor as a recycled mother liquor stream. This allows the skilled person to increase the amount of controlling acids in the oxidation reactor, if the mother liquor stream comprises controlling acids.

Preferred is a process according to the invention, wherein the oxidizable compound comprises 5-methoxymethylfurfural, and wherein the crude carboxylic acid composition comprises mono methyl ester of 2,5-furandicarboxylic acid.

It is thought that the present process can be employed for 5-alkoxymethylfurfural independent of the length of the alkoxy chain and especially for 5-alkoxymethylfurfural wherein the alkoxy group comprises 1 to 6 carbon atoms. It was found that the best results are obtained when 5-methoxymethylfurfural is employed as oxidizable compound. This is particular beneficial, because 5-methoxymethylfurfural has proven to be one of the most economically viable starting material for producing FDCA.

Preferred is a process according to the invention, wherein the mother liquor comprises mono alkyl ester of 2,5-furandicarboxylic acid, preferably mono methyl ester of 2,5-furandicarboxylic acid, in the range of 1.0 to 4% by weight with respect to the weight of the mother liquor.

The above process is preferred because we found that the above range for the amount of alkyl ester of 2,5-furandicarboxylic acid in the mother liquor ensures that the beneficial effect of the compound is strong enough to be felt while at the same time a sufficient buffer is established towards the upper limit of mono alkyl ester of FDCA that was identified, so that the process has a high flexibility with respect to variations and peaks in the concentration of the alkyl ester of 2,5-furandicarboxylic acid.

Preferred is a process wherein the mother liquor comprises bromoacetic acid, preferably in an amount of 0.5% or more by weight with respect to the weight of the mother liquor, and/or dibromoacetic acid, preferably in an amount of 0.1% or more by weight with respect to the weight of the mother liquor, and/or 5-bromo-2-furoic acid preferably in an amount of 0.02% or more by weight with respect to the weight of the mother liquor.

Depending on the chosen parameters, the mother liquor was found to comprise bromoacetic acid and/or dibromoacetic acid and/or 5-bromo-2-furoic acid. The formation of these compounds, that beneficially can act as controlling acid, was not reported for other processes of producing FDCA before, e.g. processes that start from 5-HMF, and could potentially be a characteristic feature of processes that employ 5-alkoxymethylfurfural as oxidizable compound, at least if the specific reaction conditions are established as defined above in step a).

Preferred is a process wherein the predefined threshold value for cobalt in the cake is 200 ppm by weight, preferably 50 ppm by weight, most preferred 30 ppm by weight, with respect to the weight of the 2,5-furandicarboxylic acid and/or wherein the predefined threshold value for manganese in the cake is 100 ppm by weight, preferably 25 ppm by weight, most preferred 15 ppm by weight with respect to the weight of the 2,5-furandicarboxylic acid. This process is preferred, because the respective threshold values ensure that a solid cake is obtained, that is sufficiently free of metal to allow for efficient further processing. Furthermore, preferred is a process according to the invention, wherein the predefined threshold value also includes the ratio of the weight ratio of manganese to cobalt in the cake to the weight ratio of manganese to cobalt in the catalyst system.

Preferred is a process wherein the amount of one or more controlling acids in the oxidation reactor is increased by adding the one or more controlling acids to the oxidation reactor by increasing the portion of the mother liquor which is routed to the oxidation reactor as recycled mother liquor stream.

This process is preferred because no additional controlling acids need to be handled and/or stored at the production side, thereby decreasing costs and eliminating the need for additional equipment. The amount of controlling acids in the oxidation reactor can, especially for continuous or semi-continuous processes, be increased by routing the mother liquor to the oxidation reactor as recycled mother liquor stream. If the mother liquor stream comprises one or more controlling acids, and replaces fresh solvent in the oxidation reactor, the concentration of the one or more controlling acids contained in the mother liquor will increase in the oxidation reactor. This setup allows for a sophisticated process control, wherein the amount of controlling acids in the oxidation reactor can be increased by increasing the portion of the mother liquor which is routed to the oxidation reactor as recycled mother liquor stream.

Preferred is a process according to the invention, wherein the weight ratio of cobalt to manganese in the catalyst system is 10 or higher, preferably 15 or higher, and/or wherein the weight ratio of bromine to the combined weight of cobalt and manganese in the catalyst system is 1 or higher, preferably 1.5 or higher, most preferably 2 or higher, wherein the value is preferably less than 4.0, more preferably less than 3.5. If the catalyst system comprises other metals besides cobalt and manganese in an amount of 5% by weight or more, it is preferred that the above ratios are achieved for the weight ratio of bromine to the combined weight of all metals in the catalyst system. This process is especially preferred because we found that the above catalyst system significantly outperforms other catalyst systems under the conditions defined above for step a). In particular, the inventors surprisingly found, that the respective catalyst system reduces the tendency of manganese and cobalt of the catalyst system to be incorporated into the product cake, even if increased amounts of mono alkyl ester of 2,5-furandicarboxylic acid are present and reduces the enrichment of manganese compared to cobalt in the cake. Likewise, the usage of the above catalyst system opens up a much broader range of process parameters, e.g. pressure or residence time, with that the process according to the invention can be run in a very reliable way, significantly reducing the likelihood of an undesired stop of the process and/or reducing the formation of unwanted by-products.

Preferred is a process according to the invention, wherein the isolating at least a portion of the solid 2,5-furandicarboxylic acid in a solid-liquid separation zone comprises washing the solid 2,5-furandicarboxylic acid with a washing solution comprising a saturated organic acid solvent having from 2 to 6 carbon atoms, preferably acetic acid, and less than 15%, preferably less than 10%, by weight of water. The above process is preferred because the amount of metals in the cake can further be reduced if a washing step is employed in the solid-liquid separation zone. Herein it was completely surprising that washing solutions that comprise predominantly saturated organic acid solvent, preferably acetic acid, yield reasonable success with respect to the metal removal from the cake. In the prior art it was often considered necessary to employ larger amounts of water in order to ensure sufficient metal removal from the cake. However, with the process of the present invention, the washing with organic acid was found to be sufficient to obtain sufficiently metal-free cakes. This is considered especially beneficial because larger amounts of water, that could be introduced into the system with the washing solution, are undesirable for any system that uses a mother liquor recycle into an oxidation reactor, as the oxidation reaction is often found to be sensitive to higher water concentrations.

Preferred is a process wherein the weight ratio of manganese to cobalt in the cake, divided by the weight ratio of manganese to cobalt in the catalyst system, is less than 1.5, preferably less than 1.3. This process is preferred, because it introduces a well-defined criterion for the process operator to judge, whether his process is running within the desired regime, thereby allowing for a very easy and reliable way of identifying errors in the system.

The process of the present invention requires that potentially large amounts of controlling acid are added, wherein several of these controlling acids comprise ionic bromine or bromo organic compounds. These strong acids are corrosive and can potentially form highly oxidative gaseous compounds. Correspondingly, the mother liquor stream comprises highly acetic and/or corrosive compounds and/or additional metal ions that originate from the reactor equipment, e.g. iron, nickel or chromium. Furthermore, the oxidative gaseous substances can potentially damage the overhead equipment of the oxidation reactor. Therefore, it was an additional objective of the present invention to provide counter measures for protecting the equipment, in particular the overhead equipment and the tubes that are in contact with the mother liquor stream and/or to remove unwanted metals from the mother liquor. The inventors found that the following processes are preferred that address these challenges.

Preferred is a process according to the invention, wherein the process further comprises the step:

h) contacting at least a portion of the mother liquor with a composition comprising a base selected from the group consisting of $Na_2CO_3$ and NaOH to increase the pH to more than 7, wherein one or more metal hydroxides or carbonates are precipitated from the mother liquor, wherein the metal is selected from the group consisting of cobalt, manganese, iron, nickel or chromium.

Preferred is a process wherein the mother liquor comprises cobalt in an amount greater than 2000 ppm by weight and manganese in an amount greater than 130 ppm by weight with respect to the weight of the mother liquor. This process is preferred because it enables an efficient mother liquor recycle, wherein a sufficiently high amount of catalyst metals can be preserved in the oxidation reactor based on the cobalt and manganese that is provided with the recycled mother liquor stream.

Preferred is a process wherein the solid 2,5-furandicarboxylic acid isolated in step b) is further washed with a second washing solution comprising water in an amount of more than 95%, preferably more than 99%, by weight with respect to the weight of the washing solution. This process is beneficial, as it can provide a FDCA cake that comprises a minimum amount of manganese and cobalt. However, as indicated above, the respective process is oftentimes found to be more suitable for batch processes, that do not employ mother liquor recycle. If the second washing solution is mixed with the mother liquor in the solid liquid separation zone, it becomes more difficult to reuse the mother liquor stream as the presence of large amounts of water is oftentimes undesirable in oxidation reactions as defined in step a).

Preferred is a process wherein the organic acid solvent is acetic acid. Such process is preferred because acetic acid has proven many times to be the most suitable solvent that is employed in the majority of prior art processes. Acetic acid is cheap, readily available and comparably acceptable if environmental aspects are considered.

Preferred is a process wherein the oxidizing gas comprises molecular oxygen and preferably is air. This process is preferred because the usage of air in most cases is the economically most viable way of oxidizing 5-alkoxymethylfurfural to FDCA.

Preferred is a process wherein the temperature in step a) is in the range of 170 to 190° C. This process is preferred, as the inventors found that in this specific temperature range the amount of mono alkyl ester of 2,5-furandicarboxylic acids tends to strive towards a plateau value that is well within the desired range defined above. Furthermore, the respective temperature was found to yield FDCA in high yields and with good purity as indicated qualitatively by the white cake that was found in several of the experiments that employed the respective temperatures.

Preferred is a process according to the invention, wherein the pressure in step a) is in the range of 700 to 2000 kPa, and/or wherein the oxidation reactor comprises one or more continuous stirred tank reactors, preferably two or more continuous stirred tank reactors in series. Among the possible sets of parameters and equipment tested by the inventors, the above parameters were found to be ideal for obtaining high purity FDCA in good yields while at the same time minimizing the energy costs required for pressurizing the reactors.

Preferred is a process according to the invention, wherein the solid-liquid separation zone comprises a filter or centrifuge, preferably a filter, more preferably a rotary pressure filter. The above process is beneficial, because filters and centrifuges were found to be particular suitable means for isolating the solid FDCA from the mother liquor that comprises mono alkyl ester of 2,5-furandicarboxylic acid, even though these compounds are often difficult to separate from solid FDCA.

Preferred is a process according to the invention, wherein the cake comprises 2,5-furandicarboxylic acid in an amount greater than 95%, preferably greater than 98%, by weight with respect to the weight of the dry cake and preferably mono alkyl ester of 2,5-furandicarboxylic acid in an amount in the range of 0.1 to 3%, preferably 0.15 to 2.3% by weight with respect to the weight of the dry cake, and/or wherein the cake comprises a combined amount of cobalt and manganese of less than 300 ppm, preferably less than 75 ppm, by weight with respect to the weight of the 2,5-furandicarboxylic acid in the cake.

It is thought that the amount of mono alkyl ester of FDCA should be below 3% by weight with respect to the weight of the dry cake in order to prevent a detriment for effect of this compound in subsequent purification methods.

In view of the above disclosure of the present invention, the skilled person understands that the results obtained by the inventors of the present invention also allow to define an optimized oxidation process for the production of FDCA. Such a process utilizes all the information discussed above for providing a process that can be reliably operated and provides for a low initial metal incorporation into the cake, thereby requiring less effort for process control. Correspondingly, an associated aspect of the present process can be:

Process for producing a carboxylic acid composition comprising 2,5-furandicarboxylic acid, comprising the step of:

a1) oxidizing an oxidizable compound comprising 5-alkoxymethylfurfural in an oxidation reactor in the presence of a saturated organic acid solvent having from 2 to 6 carbon atoms and a catalyst system comprising cobalt, manganese and bromine using an oxidizing gas at a temperature in the range of 160 to 210° C. to obtain a crude carboxylic acid composition comprising mono alkyl ester of 2,5-furandicarboxylic acid and solid 2,5-furandicarboxylic acid, wherein liquid phase in the reactor comprises mono alkyl ester of 2,5-furandicarboxylic acid in the range of 0.5 to 7% by weight with respect to the weight of the liquid phase, wherein the bromine is provided as hydrobromic acid, wherein the weight ratio of cobalt to manganese in the catalyst system is 10 or higher, preferably 15 or higher, and wherein the weight ratio of bromine to the combined weight of cobalt and manganese in the catalyst system is 1 or higher, preferably 1.5 or higher, most preferably 2 or higher.

It is clear to the skilled person, that preferred embodiments of this process correspond to the preferred embodiments of the process disclosed above, e.g. with respect to the solvent, the starting materials, the catalyst, the temperature, and the ranges of alkyl ester of 2,5-furandicarboxylic acid.

Hereinafter, the invention is described in more detail using experiments.

EXAMPLES

Unless described otherwise, the oxidation reactor is a 600 ml stirred pressure vessel, with two impellors. The reactor is pre-charged with a solvent comprising acetic acid and water, in a 95/5 ratio by weight, and catalyst components to make the specified composition of the catalyst system comprising cobalt, manganese and bromine. The catalyst components are provided as cobalt(II) acetate tetrahydrate, manganese (II) acetate tetrahydrate, and HBr as 48% by weight in water. The typical quantity of "pre-charge" is 310 grams.

The oxidation reactor is purged, pressurized, and heated to the desired operating temperature with stirring at 2000 rpm. The oxidizable compound provided as feed is either 5-methoxymethyl furfural (MMF) or a mixture of MMF with 5-hydroxy-methyl furfural and small amounts of levulinic acid. The process is started with a typical feed rate 8.3 mmol/minute for 60 minutes (total feed 500 mmol). A flow rate of lean air (8% oxygen) is started at a typical flow rate of 10 normal L/minute. The reaction typical begins within 3 minutes, noticed by a sharp decrease in oxygen in the outlet and an increase in CO and $CO_2$. During the reaction heat is generated, and a vapor stream is taken overhead and condensed. This vapor stream comprises mainly acetic acid and water. The amount of solvent captured in the overhead is continuously monitored, and made up in the oxidation reactor with a fresh flow of solvent to the reactor.

The typical operating pressure is 12 to 14 barg at 160° C. and 17.5 barg at 175° C.

At the end of the desired feed period, the feed of oxidizable compound is stopped, and the contents of the oxidation reaction are either "crash cooled" to room temperature (or to the desired filtration temperature) or subjected to an extended period of post-oxidation at the same reaction temperature and oxygen flow rate as given above.

Example A—Co/Mn Ratio

The experiments in example A used a MMF feed, at 160° C., with a feed for 1 hour and 15 minutes of post-oxidation. The cake was isolated by filtration and washed with 1 part solvent (95 acetic acid to 5 parts water, by weight) to 1 part estimated dry cake weight. The results are shown in table 1.

TABLE 1

Co/Mn ratios

| # | Co in cat. (ppm) | Mn in cat. (ppm) | Br in cat. (ppm) | Co in cake (ppm) | Mn in cake (ppm) |
|---|---|---|---|---|---|
| A1 | 2920 | 2820 | 6990 | 3500 | 9850 |
| A2 | 2110 | 120 | 2740 | 185 | 31 |
| A3 | 2290 | 130 | 2200 | 76 | 4 |
| A4 | 2310 | 130 | 2020 | 116 | 7 |

Table 1 shows that the present process can use different catalyst systems. High cobalt to manganese ratios seem to reduce the overall tendency of the system to incorporate metals into the cake.

Example B—Metals Ratio in Cake Vis-à-Vis Catalyst

The experiments of example B used an MMF feed at 160° C. for 1 hour and 15 minutes of post-oxidation. The catalyst was 3300 ppm Co, 185 ppm Mn, and 7000 ppm Br from aqueous HBr for all experiments. After each run the reaction slurry was cooled to 80° C. and filtered. A minimal wash of acetic acid/water (95/5 by weight) was used to displace the remaining mother liquor from the cake. The combined mother liquor and wash liquid were analyzed and corrected for cobalt, manganese, ionic bromine, and water (5%). This material was then used as the pre-charge for the next run, in order to simulate a recycle operation. In consequence, subsequent experiments were conducted with an increased amount of controlling acid in the oxidation reactor. The cobalt recovery in each case was 90-95%, allowing for high recycle content. The recycle in each case used the mother liquor from the previous run as the pre-charge, after adjusting to make catalyst to the desired level.

A total of 8 runs were made, with a total of 7 recycles. Table 2 shows both the cake quality and the mother liquor composition. The yield is the combined yield of FDCA and monoester of FDCA recovered in the cake. The results are summarized in table 2.

The result shows that in run B 1, i.e. the fresh feed run (no recycle), the Mn/Co ratio of the cake divided by the same ratio in the catalyst is very high, indicating excessive precipitation of Mn into the cake (often associated with pink cake). Furthermore, relatively high amounts of Co and Mn were detected in the cake. The remaining runs, all of which include some FDCA-Me and controlling acids by virtue of the recycle (bromoacetic acid, dibromoacetic acid, acetoxyacetic acid, 5-bromo-2-furoic acid, and fumaric acid), had yields which stayed constant and showed no excess manganese over cobalt precipitation.

FDCA-Me was found to consistently build up with each recycle. The experimental set-up did not allow for a further significant increase of the controlling acid, as only the mother liquor was used in each case and build-up of the acids at some point is governed by the steady state achieved between new production and removal. It can be seen that the amount of metals in the cake decreases to highly desirable values as both the concentration of FDCA-Me and controlling acid initially rise in experiments B2 to B4. Further, the ratio of Mn/Co in the cake to that in the catalyst feed is consistently near unity, showing that excess metal (Mn) was not incorporated in the cake. However, while the amount of controlling acids plateaus, the build-up of FDCA-Me continues and its detrimental effect on the metal incorporation apparently starts to dominate the system. We observed increased filtration difficulty when levels of FDCA-Me were very high. In this case the metals stay at the same ratio as in the catalyst feed but are comparably high, indicating a problem with obtaining good washing and respective removal of the mother liquor.

Example C—Different Feeds

The experiments in example C were run in the same manner as for example B but used a feed comprising a mixture of 5-HMF (6.4 wt %), MMF (86.4 wt %), and a small quantity of levulinates (2.3 wt %) with minor amounts of other compounds. The recycle rate was 90+% for each of the runs C2 to C4. The results are summarized in table 3.

TABLE 2

Mn/Co ratio in cake vis-a-vis catalyst

| | Cake properties | | | | Mother liquor properties | | | |
|---|---|---|---|---|---|---|---|---|
| # | Yield (mol %) | Co (ppm) | Mn (ppm) | Mn/Co cake/cat. | FDCA-Me (wt %) | Br-acetic acid (wt %) | Dibromo-acetic acid (wt %) | Acetoxy-acetic acid (wt %) | Fumaric acid (wt %) |
| B1 | 81.3 | 209 | 62 | 5.3 | 1.24 | 0.38 | 0.02 | 0.09 | 0.16 |
| B2 | 79.8 | 154 | 9 | 1.0 | 2.50 | 0.64 | 0.05 | 0.16 | 0.26 |
| B3 | 79.2 | 67 | 4 | 1.1 | 3.34 | 0.77 | 0.07 | 0.16 | 0.33 |
| B4 | 78.7 | 88 | 5 | 1.0 | 4.10 | 0.85 | 0.09 | 0.18 | 0.38 |
| B5 | 79.4 | 302 | 17 | 1.0 | 4.72 | 0.95 | 0.11 | 0.24 | 0.44 |
| B6 | 79.6 | 354 | 18 | 0.9 | 4.96 | 0.92 | 0.08 | 0.26 | 0.40 |
| B7 | 79.4 | 301 | 16 | 0.9 | 5.40 | 0.93 | 0.10 | 0.29 | 0.51 |
| B8 | 80.0 | 639 | 31 | 0.9 | 5.76 | 0.87 | 0.07 | 0.25 | 0.49 |

TABLE 3

Different feeds

| | Cake properties | | | | Mother liquor properties | | | | |
|---|---|---|---|---|---|---|---|---|---|
| | | | | | | Br- | Dibromo- | Acetoxy- | |
| # | Yield (mol %) | Co (ppm) | Mn (ppm) | Mn/Co cake/ cat. | FDCA-Me (wt %) | acetic acid (wt %) | acetic acid (wt %) | acetic acid (wt %) | Fumaric acid (wt %) |
| C1 | 87.2 | 163 | 54 | 5.9 | 1.30 | 0.31 | 0.08 | 0.02 | 0.23 |
| C2 | 86.4 | 29 | 1 | 0.6 | 2.43 | 0.53 | 0.09 | 0.03 | 0.42 |
| C3 | 86.9 | 23 | 1 | 0.8 | 3.83 | 0.65 | 0.13 | 0.05 | 0.52 |
| C4 | 81.7 | 45 | 1 | 0.4 | 4.82 | 0.53 | 0.19 | n.d. | 0.59 |

As in example B, the first run, i.e. made without the addition of highly acidic components, resulted in a high level of manganese in the cake. In runs C2 to C4, which included controlling acids in the oxidation reactor, the yield was good and the total amount of metals in the cake were low. The experiments exemplify the process of the present invention for different feed compositions. In particular, mixtures of 5-HMF and MMF gave good results.

Example D—Temperature

The experiments in example D were run using the same feed as the experiments C, but at a temperature of 175° C. (except for the first two runs at 160° C.). The recycle rate was set at 80% of mother liquor, based on cobalt as a standard. A 1-hour post-oxidation, also at 175° C., was used. The pressure was increased to 17.5 barg to adapt to the higher temperature and solvent vapor pressure. The first two runs were made at 160° C. in order to build a "mother liquor" composition for the high temperature experiments. The results are summarized in Table 4.

TABLE 4

Temperature

| | Cake properties | | | | Mother liquor properties | | | | | |
|---|---|---|---|---|---|---|---|---|---|---|
| | | | | | | Br- | Dibromo- | Acetoxy- | | |
| # | Yield (mol %) | Co (ppm) | Mn (ppm) | Mn/Co cake/ cat. | FDCA-Me (wt %) | acetic acid (wt %) | acetic acid (wt %) | acetic acid (wt %) | Fumaric acid (wt %) | 5-Br-2 FCA (wt %) |
| D1 | 81.9 | 306 | 70 | 4.1 | 1.42 | 0.25 | 0.10 | 0.10 | 0.24 | 0.02 |
| D2 | 84.2 | 16 | 1 | 1.1 | 2.60 | 0.39 | 0.18 | 0.15 | 0.37 | 0.03 |
| D3 | 79.3 | 301 | 60 | 3.6 | 2.26 | 0.47 | 0.12 | 0.20 | 0.38 | 0.04 |
| D4 | 81.7 | 14 | 1 | 1.3 | 2.45 | 0.49 | 0.14 | 0.21 | 0.44 | 0.04 |
| D5 | 81.2 | 27 | 2 | 1.3 | 2.57 | 0.51 | 0.15 | 0.23 | 0.47 | 0.05 |
| D6 | 80.6 | 24 | 2 | 1.5 | 2.50 | 0.45 | 0.13 | 0.22 | 0.44 | 0.05 |
| D7 | 80.4 | 12 | 1 | 1.5 | 2.10 | 0.45 | 0.15 | 0.20 | 0.45 | n.d. |

Similar to examples B and C, the first run with no added controlling acids gave a very high level of manganese in the cake. Again, the first run with increased amount of controlling acid in the oxidation reactor (still at 160° C.) provides excellent metal contents in the cake, even with comparably low amounts of controlling acids. The third run, which is the first at 175° C., has a somewhat elevated level of manganese in the cake which could be attributed to the new steady state of the process with respect to its mother liquor composition that establishes at the increased temperature. In other words, it is suspected that D3 would exhibit even more metals in the cake if it were conducted without controlling acids. In fact, the process is expected to die when runs were directly attempted at 170° C. without adding controlling acids. The first two runs were made at 160° C. in order to build a system which lived. The subsequent runs all show the desired low level of metals in the cake and provide excellent yields and surprisingly low amount of metal in the cake, even for the last run. It can be seen that the mono ester content levelled out at a lower level when running at 175° C. with post oxidation and 80% recycle compared to the full recycle runs at 160° C. with no post-oxidation. Together with the other experiments this shows that excellent results can be achieved over several runs if the mono ester content is managed. Furthermore, the beneficial effect of the controlling acids is again confirmed by Example D.

Example E—Effect of Bromine Content

The experiments of Example E were run using the same set-up as described above. The feed used was purified 5-methoxymethylfurfural (MMF), using a total of 500 mmol of MMF, that was fed at a steady rate over a total of 1 hour. The reaction temperature was 160° C., and the pressure was 12 barg. No post-oxidation was used. The reactor "precharge" was 310 grams, with catalyst and added alkyl monoester of FDCA (FDCA-Me) as noted below. The total yield reported is the sum of FDCA and FDCA-Me, after subtracting the initial FDCA-Me, on a molar basis relative to the MMF feed. Beside the exact measurements, the cake colour was used as qualitative indicator for the concentration of manganese in the cake (from white to pink scale) and the concentration of undesired side-products and colour bodies (from white to yellow to brown scale). These qualitative analysis is fast and provides a quite reliable impression of the cake quality as even minor amounts of impurities result in a notable colouration of the cake. The results are summarized in table 5.

TABLE 5

Effect of bromine content

| # | Co/Mn/Br ppm | Initial FDCA-Me, wt % | Total yield, mol % | Cake Co, ppm | Cake Mn, ppm | Mn/Co cake/cat | Cake colour |
|---|---|---|---|---|---|---|---|
| E1 | 2200/125/2000 | 0 | 82.6 | 1771 | 466 | 4.6 | Light pink |
| E2 | 2200/125/2000 | 3 | 78.7 | 848 | 41 | 0.9 | Yellow |
| E3 | 2200/125/2000 | 6 | 73.3 | 2554 | 128 | 0.9 | Yellow-brown |
| E4 | 2200/125/2000 | 9 | 62.4 | 2558 | 124 | 0.9 | Brown |
| E5 | 3300/185/3000 | 0 | 82.3 | 9057 | 1067 | 2.1 | Pink |
| E6 | 3300/185/7000 | 0 | 90.2 | 74 | 13 | 3.1 | White |
| E7 | 3300/185/7000 | 6 | 90.1 | 294 | 14 | 0.8 | White-yellow |
| E8 | 3300/185/7000 | 6 | 83.5 | 2774 | 147 | 0.9 | Yellow |
| E9 | 3300/185/7000 | 6 | 86.4 | 1420 | 73 | 0.9 | White |

Comparing E1 and E2, or E6 and E7-E9, shows that FDCA-Me seems to reduce the problem of manganese enrichment in the cake, as evidenced by both the reduced absolute values as well as the drop in the Mn/Co cake/catalyst ratio, from numbers well above 1 with no added FDCA-Me, to numbers near or below 1 with the added FDCA-Me. However, E1 to E4 show that excess of FDCA-Me adversely affects the process, wherein the process of E4, that gives a brown product, can be considered a failure. This example also suggests that good washing of the cake is more difficult with excess of FDCA-Me present, as indicated by an elevated level of both metals despite a Mn/Co cake/catalyst ratio near unity. Comparison of E5 and E6 proves that the addition of additional Br as hydrobromic acid significantly reduces the amount of manganese in the cake. Furthermore, E5 died prematurely, with only 362 mmol of feed (out of planned 500 mmol) when the reaction suddenly died, whereas E6 ran without problems. Based on these results, it can be deduced that HBr can function as a controlling acid within the meaning of the present invention. In fact, it can be seen that the catalyst system employed in E6 to E9 is an optimized catalyst system for the oxidation of 5-alkoxymethylfurfural. While E3 gives a yellow-brown cake at 6 wt % FDCA-Me, the colour of the cake in E7 to E9 does not reach brown-level. Instead, even "white" cakes can be obtained in E9. Finally, the yields in E6 compared to E1, or in E7-E9 compared to E3, are also substantially increased.

Example F—Controlling Acids

The experiments of example F were run using the same set-up as described above. The feed used was purified 5-methoxymethylfurfural (MMF), using a total of 500 mmol of MMF, that were fed at a steady rate over a total of 1 hour. The reaction temperature was 160° C., and the pressure was 12 barg. No post-oxidation was used. The reactor "precharge" was 310 grams, with catalyst and added components as noted below. The total yield reported is the sum of FDCA and FDCA-ME, after subtracting any initial FDCA-ME, on a molar basis relative to the MMF feed. The catalyst in all cases was 3300 ppm cobalt, 185 ppm manganese and 7000 ppm bromine. The results are summarized in table 6 wherein a pink cake was observed for experiments F4 and F7.

TABLE 6

Controlling acids

| # | Added component, | Added component, wt % | pKa | Total yield, mol % | Cake Co, ppm | Cake Mn, ppm | Mn/Co cake/catalyst |
|---|---|---|---|---|---|---|---|
| F1 | none | — | — | 90.2 | 74 | 13 | 3.1 |
| F2 | Fumaric acid | 1.1 | 3.03 | 85.2 | 30 | <0.5 | 0.3 |
| F3 | Bromoacetic acid | 1.3 | 2.86 | 91.6 | 76 | 2 | 0.5 |
| F4 | Formic acid | 1.5 | 3.77 | 88.7 | 1704 | 494 | 5.2 |
| F5 | Maleic acid | 1.1 | 1.9 | 88.1 | 99 | 9 | 1.6 |
| F6 | 2-Furoic acid | 1.1 | 3.16 | 85.0 | 144 | 6 | 0.7 |
| F7 | FFCA | 1.4 | 2.57 (est) | 75.4 | 711 | 259 | 6.5 |

Not all acids that were added in the experiments resulted in the desired white cake which was also low in precipitated metals and free of manganese enrichment, as evidenced by the Mn/Co cake/catalyst ratio. The reference case (no controlling acids added) used the robust catalyst system identified before and had a relatively white cake but still showed unwanted manganese enrichment in the cake. The addition of formic acid and 2-carboxy-5-(formyl)furan (FFCA) did not yield the desired white cake or the desired low value of Mn/Co cake/catalyst. Considering that a white cake can be obtained with this catalyst set-up in some cases even if no controlling acid was added, it was concluded that the respective acids might even have a detrimental effect. Each of the other acids in the table had a positive impact on reducing the Mn/Co cake/catalyst ratio, evidence that they are suitable for reducing the problem of excessive manganese in the cake. In most cases the overall metals content was also good, showing also a good washability of the cake. Taking into account all experimental evidence, it was deduced that suitable controlling acids are selected from the group consisting of hydrobromic acid and mono- or dicarboxylic acids having from 2 to 5 carbon atoms and a pKa of less than 3.2.

Example G—Addition of HBr of Bromoacetic Acid

The experiments of example G were run using the same set-up as described above. The feed is a mixture of 5-HMF (6.4 wt %), MMF (86.4 wt %), and a small quantity of levulinates (2.3 wt %), with minor amounts of other compounds. In each case the reactor was "pre-charged" with 310 grams of 95/5 acetic acid/water by weight and catalyst compositions as noted. The reactor temperature was 170° C. The catalyst in all cases was Co/Mn/Br at 3300/185/7000 ppm by weight, with bromine provided using an aqueous solution of HBr. It was observed that the catalyst composition which ran well at 160° C., allowing the full 1 hour feed for a total of 500 mmol, would not run for the entire hour at a temperature of 170° C., and a pressure of 17-18 barg. At some point in the course of the run it would be observed that the reaction abruptly stopped, as evidenced by a rapid increase in the oxygen content of the outlet gas stream, and reduction in $CO_2$ and CO production.

TABLE 7

Addition of HBr or bromoacetic acid

| # | Added compound | Lived/died | Cake colour | Yield, FDCA + FDCA-ME, mol % |
|---|---|---|---|---|
| G1 | None | Died | N.D. | N.D. |
| G2 | mother liquor from 160° C. run | Lived | Pink | 89% |
| G3 | 1.6 wt % bromoacetic acid | Lived | White | 92% |
| G4 | 1.9 wt % FDCA | No initiation | N.A. | N.A. |
| G5 | HBr, to total 8500 ppm | Lived | White | approx 87% |

In experiment G1 (no acid added), the process died without allowing for a meaningful analysis of yields and cake colour. In experiment G4 (no FDCA added), it was not possible to initiate the process. In G2 mother liquor from a previous run was added, thereby increasing the amount of FDCA-Me and controlling acids in the oxidation reactor (at a relatively low amount). While G2 showed significant manganese incorporation in the cake, it resulted in a living process with acceptable yields. In experiment G3 (addition of bromoacetic acid) and experiment G5 (addition of HBr), a living process gave a desirable white cake, indicating low manganese amounts.

Example H—Addition of HBr

This example was run using a single continuous stirred tank oxidation reactor (CSTR). The levels of cobalt and manganese were held constant throughout, and feeds with different levels of HBr were processed, in order to observe the effect of added HBr on the system.

The reactor is fitted with a reflux condenser and a pump in order to allow heat removal via the evaporation of solvent, while pumping the reflux back to the reactor. The reactor was pre-charged with approximately 100 gram of the specified catalyst package in acetic acid. The reactor was heated to 160° C. under a pressure of nitrogen. After reaching temperature the gas was switched to mixture of air and nitrogen, comprising 8% oxygen, at a flow rate of 3.3 Nl/min. Feed of 20 wt % "RMF" (a mixture of 5-HMF, MMF, and levulinics as used previously) in acetic acid with the desired cobalt and manganese (3000 ppm and 300 ppm, respectively). The feed contains a total of approximately 1 wt % water, and this establishes a steady state concentration in the rector of about 6%, due to water formed during the oxidation. A valve at the bottom of the reactor opens approximately every 30 seconds, removing a small amount of material, in order to keep a constant level and to establish "CSTR" conditions. The temperature was maintained at 160° C., with a pressure of 13 barg, and a residence time of 60 minutes. After at least 3 hours time-on-stream the reactor was considered to be at steady state and sampling could begin. At the end of each run the feed was shut off and a post-oxidation was conducted. Following the post-oxidation the reactor was cooled and the contents filtered, washed with acetic acid/water, and dried before analysis. The table below shows the metal content of the cakes.

TABLE 8

Addition of HBr

| Run | Bromine in feed, ppm | Bromine/(Co + Mn) weight/weight | Cake Co, ppm | Cake Mn, ppm | Mn/Co cake/catalyst |
|---|---|---|---|---|---|
| H1 | 514 | 0.16 | 2705 | 1100 | 4.1 |
| H2 | 2023 | 0.61 | 1246 | 593 | 4.8 |
| H3 | 4475 | 1.36 | 98 | 14 | 1.4 |
| H4 | 5998 | 1.82 | 35 | 4 | 1.2 |
| H5 | 6996 | 2.12 | 29 | 4 | 1.6 |
| H6 | 8879 | 2.69 | 16 | 2 | 1.2 |

The runs H1 and H2 show both a high overall level of metals in the cake and also a high value for the ratio of Mn/Co cake/catalyst. The remaining runs all have low overall metals incorporation, getting lower as HBr was increased, and all show a very good ratio, near unity, for Mn/Co cake/catalyst.

The invention claimed is:

1. A process for producing a carboxylic acid composition comprising 2,5-furandicarboxylic acid, comprising the steps:
   a) oxidizing an oxidizable compound comprising 5-alkoxymethylfurfural in an oxidation reactor in the presence of a saturated organic acid solvent having from 2 to 6 carbon atoms and a catalyst system comprising cobalt, manganese and bromine using an oxidizing gas at a temperature in the range of 160 to 210° C. to obtain a crude carboxylic acid composition comprising mono alkyl ester of 2,5-furandicarboxylic acid and solid 2,5-furandicarboxylic acid,
   b) isolating at least a portion of the solid 2,5-furandicarboxylic acid from the crude carboxylic acid composition in a solid-liquid separation zone to generate a solid cake and a mother liquor,
   c) determining the amount of manganese and/or cobalt in the cake, and
   d) increasing the amount of one or more controlling acids in the oxidation reactor, if the determined amount of manganese and/or cobalt in the cake exceeds a predefined threshold value,
   wherein the one or more controlling acids are selected from the group consisting of hydrobromic acid and mono— or dicarboxylic acids having from 2 to 5 carbon atoms and a pKa of less than 3.2, and
   wherein the mother liquor comprises mono alkyl ester of 2,5-furandicarboxylic acid in the range of 0.5 to 7% by weight with respect to the weight of the mother liquor.

2. The process according to claim 1, wherein the one or more controlling acids are selected from the group consisting of hydrobromic acid, bromoacetic acid, dibromoacetic acid, 5-bromo-2-furoic acid, fumaric acid, acetoxy-acetic acid, maleic acid and furoic acid.

3. The process according to claim 1, wherein the process of producing a carboxylic acid composition is a continuous process wherein at least 60% by weight, of the mother liquor is routed from the solid-liquid separation zone to the oxidation reactor as recycled mother liquor stream.

4. The process according to claim 1, wherein the oxidizable compound comprises 5-methoxymethylfurfural, and wherein the crude carboxylic acid composition comprises mono methyl ester of 2,5-furandicarboxylic acid.

5. The process according to claim 1, wherein the mother liquor comprises mono alkyl ester of 2,5-furandicarboxylic acid in the range of 1.0 to 4% by weight with respect to the weight of the mother liquor.

6. The process according to claim 1, wherein the mother liquor comprises bromoacetic acid and/or dibromoacetic acid and/or 5-bromo-2-furoic acid.

7. The process according to claim 1, wherein the predefined threshold value for cobalt in the cake is 200 ppm by weight with respect to the weight of the 2,5-furandicarboxylic acid and/or wherein the predefined threshold value for manganese in the cake is 100 ppm by weight, with respect to the weight of the 2,5-furandicarboxylic acid.

8. The process according to claim 3, wherein the amount of one or more controlling acids in the oxidation reactor is increased by adding the one or more controlling acids to the oxidation reactor by increasing the portion of the mother liquor which is routed to the oxidation reactor as recycled mother liquor stream.

9. The process according to claim 1, wherein the weight ratio of cobalt to manganese in the catalyst system is 10 or higher and/or wherein the weight ratio of bromine to the combined weight of cobalt and manganese in the catalyst system is 1 or higher.

10. The process according to claim 1, wherein the isolating at least a portion of the solid 2,5-furandicarboxylic acid in a solid-liquid separation zone comprises washing the solid 2,5-furandicarboxylic acid with a washing solution comprising acetic acid, and less than 15%; by weight of water.

11. The process according to claim 1, wherein the solid 2,5-furandicarboxylic acid isolated in step b) is further washed with a second washing solution comprising water in an amount of more than 95% by weight with respect to the weight of the washing solution.

12. The process according to claim 1, wherein the temperature in step a) is in the range of 170 to 190° C.

13. The process according to claim 1, wherein the pressure in step a) is in the range of 700 to 2000 kPa, and/or wherein the oxidation reactor comprises one or more continuous stirred tank reactors.

14. The process according to claim 1, wherein the ratio of the weight ratio of manganese to cobalt in the cake to the weight ratio of manganese to cobalt in the catalyst system is less than 2.5.

15. The process according to claim 1, wherein the cake comprises 2,5-furandicarboxylic acid in an amount greater than 95% by weight with respect to the weight of the dry cake.

16. The process according to claim 5, wherein the mother liquor comprises mono methyl ester of 2,5-furandicarboxylic acid in the range of 1.0 to 4% by weight with respect to the weight of the mother liquor.

17. The process according to claim 6, wherein the mother liquor comprises bromoacetic acid in an amount of 0.5% or more by weight with respect to the weight of the mother liquor, and/or dibromoacetic acid in an amount of 0.1% or more by weight with respect to the weight of the mother liquor, and/or 5-bromo-2-furoic acid in an amount of 0.02% or more by weight with respect to the weight of the mother liquor.

18. The process according to claim 14, wherein the ratio of the weight ratio of manganese to cobalt in the cake to the weight ratio of manganese to cobalt in the catalyst system is less than 2.

19. The process according to claim 18, wherein the ratio of the weight ratio of manganese to cobalt in the cake to the weight ratio of manganese to cobalt in the catalyst system is less than 1.5.

20. The process according to claim 15, wherein the cake comprises mono alkyl ester of 2,5-furandicarboxylic acid in an amount in the range of 0.1 to 3%.

21. The process according to claim 20, wherein the cake comprises 2,5-furandicarboxylic acid in an amount greater than 98% by weight with respect to the weight of the dry cake and mono alkyl ester of 2,5-furandicarboxylic acid in an amount in the range of 0.15 to 2.3% by weight with respect to the weight of the dry cake.

* * * * *